(12) United States Patent
Surace

(10) Patent No.: US 10,004,632 B2
(45) Date of Patent: Jun. 26, 2018

(54) DEVICES, SYSTEMS, AND KITS FOR REGULATING SKIN TEMPERATURE FOR MAMMALS

(71) Applicant: Slumber Science LLC, Sunnyvale, CA (US)

(72) Inventor: Kevin Surace, Sunnyvale, CA (US)

(73) Assignee: SLUMBER SCIENCE LLC, Sunnyvale, CA (US)

( * ) Notice: Subject to any disclaimer, the term of this patent is extended or adjusted under 35 U.S.C. 154(b) by 31 days.

(21) Appl. No.: 15/213,061

(22) Filed: Jul. 18, 2016

(65) Prior Publication Data

US 2017/0014266 A1 Jan. 19, 2017

Related U.S. Application Data

(60) Provisional application No. 62/193,363, filed on Jul. 16, 2015, provisional application No. 62/205,884, filed on Aug. 17, 2015.

(51) Int. Cl.
| | |
|---|---|
| F25B 21/02 | (2006.01) |
| A61F 7/02 | (2006.01) |
| A61F 7/00 | (2006.01) |
| F25D 3/08 | (2006.01) |
| F25D 31/00 | (2006.01) |
| A41D 13/005 | (2006.01) |

(52) U.S. Cl.
CPC ............... *A61F 7/02* (2013.01); *A61F 7/007* (2013.01); *F25B 21/02* (2013.01); *F25D 3/08* (2013.01); *A41D 13/005* (2013.01); *A61F 2007/0007* (2013.01); *A61F 2007/0042* (2013.01); *A61F 2007/0075* (2013.01); *A61F 2007/0292* (2013.01); *F25B 2321/0251* (2013.01); *F25D 31/005* (2013.01); *F25D 2400/26* (2013.01)

(58) Field of Classification Search
CPC ... A61F 2007/0075; F25B 21/02; H01L 35/30
USPC .......................................... 62/3.2, 3.5, 259.3
See application file for complete search history.

(56) References Cited

U.S. PATENT DOCUMENTS

| | | | | |
|---|---|---|---|---|
| 3,548,415 | A | * | 12/1970 | Waters .................... A42B 3/286 165/46 |
| 3,889,684 | A | * | 6/1975 | Lebold ...................... A61F 7/02 607/109 |
| 4,381,025 | A | * | 4/1983 | Schooley .................. A61F 7/03 224/219 |
| 4,470,263 | A | | 9/1984 | Lehovec et al. |
| 4,483,021 | A | | 11/1984 | McCall |

(Continued)

FOREIGN PATENT DOCUMENTS

WO 2014/078630 A1 5/2014

*Primary Examiner* — Melvin Jones
(74) *Attorney, Agent, or Firm* — Ascenda Law Group, PC

(57) ABSTRACT

A heat transfer system may include a heat transfer machine adapted to thermally couple to an heat transfer pack housed within an heat transfer device and transfer heat from the heat transfer pack using a power supply. The heat transfer device may include a housing and a heat transfer pack. The heat transfer pack may be adapted to thermally couple to the heat transfer machine, transfer heat to the heat transfer machine while thermally coupled to the heat transfer machine, and transfer heat from a mammal's skin when the heat transfer device is in contact with the mammal's skin and uncoupled from the heat transfer machine.

27 Claims, 12 Drawing Sheets

(56) References Cited

U.S. PATENT DOCUMENTS

| | | | |
|---|---|---|---|
| 4,854,319 A * | 8/1989 | Tobin | A61F 7/10 |
| | | | 2/171.2 |
| 5,119,513 A * | 6/1992 | McKay | A41D 20/005 |
| | | | 2/170 |
| 5,353,605 A | 10/1994 | Naaman | |
| 5,623,828 A | 4/1997 | Harrington | |
| 5,800,490 A | 9/1998 | Patz et al. | |
| 5,867,999 A | 2/1999 | Bratton et al. | |
| 6,297,728 B1 | 10/2001 | Rippbauer | |
| 6,402,776 B1 | 6/2002 | Martin | |
| 7,156,867 B2 | 1/2007 | Lennox | |
| 8,236,038 B2 | 8/2012 | Nofzinger | |
| 8,267,983 B2 | 8/2012 | Rogers et al. | |
| 8,425,583 B2 | 4/2013 | Nofzinger | |
| 8,529,613 B2 | 9/2013 | Radziunas et al. | |
| 9,089,400 B2 | 7/2015 | Nofzinger | |
| 9,211,212 B2 | 12/2015 | Nofzinger et al. | |
| 2007/0250138 A1 | 10/2007 | Nofzinger | |
| 2009/0054958 A1 | 2/2009 | Nofzinger | |
| 2010/0005572 A1 | 1/2010 | Chaplin | |
| 2011/0125238 A1 | 5/2011 | Nofzinger | |
| 2013/0019611 A1 | 1/2013 | Sims et al. | |
| 2013/0238063 A1 | 9/2013 | Nofzinger | |
| 2014/0137569 A1 | 5/2014 | Parish et al. | |
| 2014/0312834 A1 | 10/2014 | Tanabe et al. | |
| 2015/0018905 A1 | 1/2015 | Nofzinger et al. | |
| 2015/0290420 A1 | 10/2015 | Nofzinger | |
| 2016/0128864 A1 | 5/2016 | Nofzinger et al. | |

\* cited by examiner

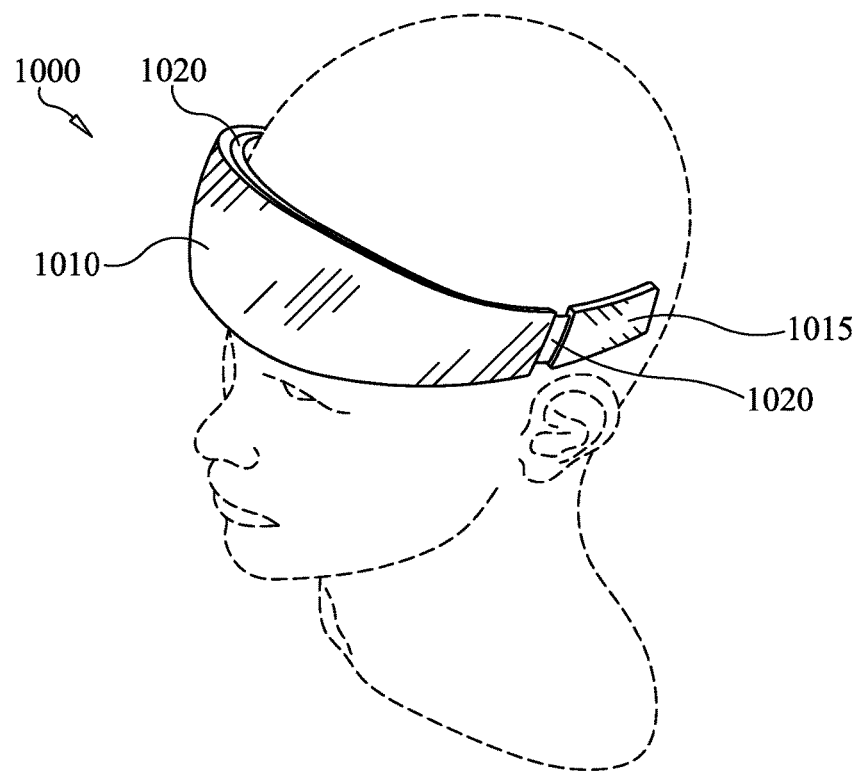
FIG. 12
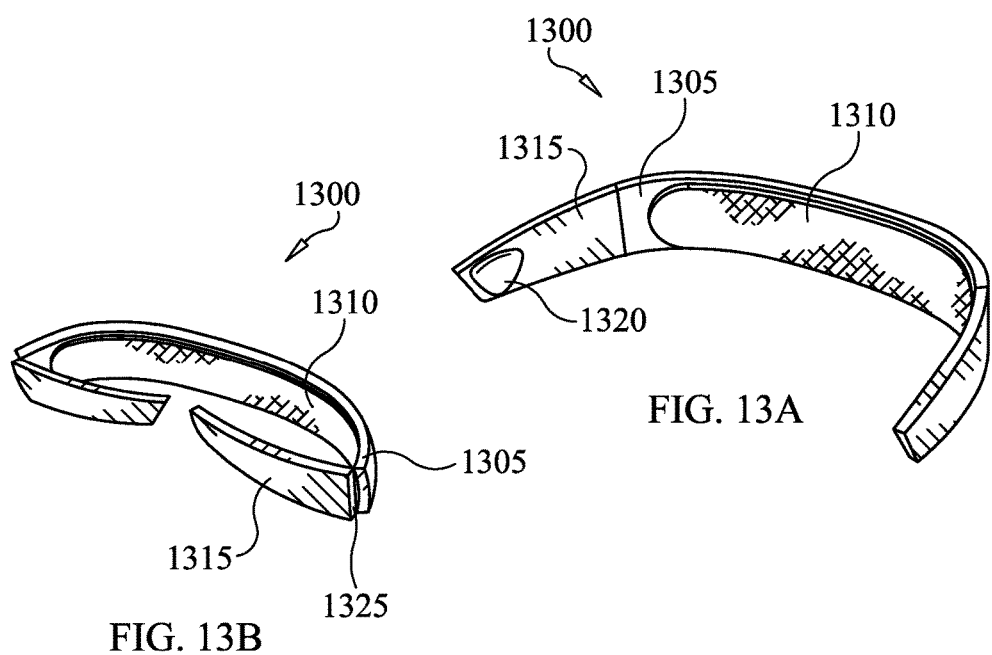
FIG. 13A
FIG. 13B

DEVICES, SYSTEMS, AND KITS FOR REGULATING SKIN TEMPERATURE FOR MAMMALS

RELATED APPLICATIONS

This application is a NON-PROVISIONAL of U.S. Patent Application No. 62/193,363 filed Jul. 16, 2015 and of U.S. Patent Application No. 62/205,884 filed Aug. 17, 2015, all of which are incorporated herein by reference.

BACKGROUND

Traditional cold packs used to transfer heat from mammalian skin utilize either a chemical reaction or a refrigerator/freezer to chill a substance, which is usually water or gel. These packs are difficult to use because, for example, a refrigerator is not portable. Therefore, if a user wants a cold pack, he or she must travel to the refrigerator to extract the pack. Furthermore, the user has no control over the temperature of the cold pack other than by controlling the temperature of the refrigerator, which may not be convenient.

Traditional hot packs are problematic in that they typically require an electrical connection, as may be the case with a heating pad, and offer poor temperature regulation.

SUMMARY

Disclosed herein is a heat transfer system that may include a heat transfer machine adapted to thermally couple to a heat transfer pack housed within a heat transfer device and transfer heat from the heat transfer pack using a power supply. The housing may be adapted to house the heat transfer pack and conform to a portion of a mammal's skin. The heat transfer pack may be adapted to thermally couple to the heat transfer machine, transfer heat to the heat transfer machine while thermally coupled to the heat transfer machine, and transfer heat from a mammal's skin when the heat transfer device is in contact with the mammal's skin and uncoupled from the heat transfer machine. The heat transfer device may be configured to be worn on at least one of a mammal's head, arm, leg, torso, hand, and foot. The heat transfer machine may be adapted to transfer heat from the heat transfer pack and thereby achieve a desired temperature for the heat transfer pack within a range of for example, 1 to 10 hours.

In some embodiments, the heat transfer system may include a Peltier device, a metal plate, a heat sink adapted to absorb heat from the Peltier device, and a fan adapted to dissipate heat from the heat sink, and a power supply. On some occasions, the heat transfer machine may be adapted to power off when the heat transfer pack is no longer thermally coupled to the heat transfer machine.

In some embodiments, the heat transfer machine may be adapted to transfer heat to the heat transfer pack and the heat transfer pack may be adapted to transfer heat to the mammal's skin. The heat transfer machine may be adapted to transfer heat from the heat transfer pack via conduction.

The heat transfer pack may be removably attached to the heat transfer device and in some instances may not be electrically coupled to the heat transfer machine. The heat transfer pack may include one or more phase change materials. In some embodiments, the heat transfer pack may be cooled to a temperature within the range of for example, 1° C. and 9° C.

The heat transfer pack may be positioned on an external surface of the heat transfer machine and, in some instances, may maintain its temperature for at least 20 minutes when in contact with the mammal's skin and up to 3 hours.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 10-12 provide exemplary heat transfer devices, in accordance with some embodiments of the present invention;

FIGS. 13A-13D provide different views of another exemplary heat transfer devices, in accordance with some embodiments of the present invention;

DETAILED DESCRIPTION

Figure 1A:
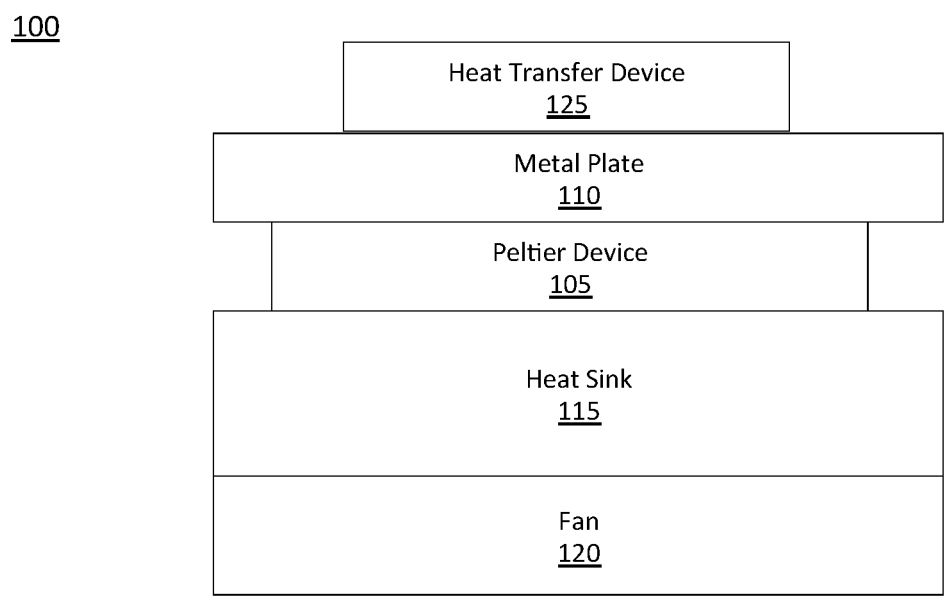
FIGS. 1A and 1B are block diagrams that illustrate exemplary heat transfer systems, in accordance with some embodiments of the present invention.

Disclosed herein is a system for cooling and/or heating the skin of a mammal (e.g., human being, cat, dog, horse, etc.). The system includes two fundamental components, a heat transfer machine and a heat transfer device. It is intended that the heat transfer machine be a machine that cools and/or heats the heat transfer device using a power supply (e.g., battery or electricity). Once the heat transfer device is heated and/or cooled, it may be removed from the heat transfer device and applied to the mammalian skin so as to heat and/or cool the mammalian skin. In most instances, the heat transfer device will be untethered to the heat transfer machine when applied to the mammal's skin. In one embodiment, the heat transfer machine is a tabletop device that may be placed on a user's nightstand so as to provide ready access to a chilled and/or heated heat transfer device during the night. In other embodiments, a heat transfer device may be used to regulate body temperature and may thusly provide comfort cooling for an individual that is not directed toward treatment of an injury as a traditional ice pack may be.

In most embodiments, the heat transfer device will rest on top of and/or outside of the heat transfer machine and/or a component of the heat transfer machine that provides heat transfer capability. When the heat transfer device is cooled, it may be cooled to a desired temperature of for example, 1-9° C. The heat transfer device and/or a heat transfer pack situated thereon may be adapted to maintain a desired temperature when in contact with mammalian skin for a period of time (e.g., 20 minutes, 1 hour, 3 hours, etc.). The heat transfer pack's ability to maintain a desired temperature when in contact with the mammalian skin may be achieved by, for example, the use of desired materials and/or combinations of materials for the heat transfer device, heat transfer pack, and/or heat transfer machine.

Typically, heat transfer devices include a housing configured to house one or more heat transfer packs and may be adapted to be positioned on mammalian skin in a particular location. For example, a heat transfer device housing may be configured to be worn on a mammal's head, leg, ankle, knee, elbow, etc. Exemplary heat transfer device housings may be made from rigid, semi-rigid, and/or flexible materials and, in some instances, may include one or more fastening mechanisms (e.g., VELCRO™, clips, elastic, snaps, etc.). On some occasions, heat transfer device housings may include an insulation layer adapted to, for example, transfer heat to and/or from the mammalian skin more efficiently, absorb condensation or sweat, increase the comfort of wearing an heat transfer device, provide a source of friction between the heat transfer device and the mammal's skin so as to prevent movement and/or slipping of the heat transfer device from it's desired location, etc.

Heat transfer packs may be any material configured to change temperature when placed in or on a heat transfer machine including, but not limited to, gel, cellulose solutions with a freezing point of approximately 32° F., silica gel solutions with an exemplary freezing point of approximately 25° F., a cryopak phase change material (PCM) with a freezing point of approximately 40° F., diethylene glycol with a freezing point between approximately 10° F. and 32° F., ethylene glycol with a freezing point between approximately 8° F. and 32° F., moldable clay, and water.

In some instances, heat transfer packs may be removable from the heat transfer device housing via one or more attachment mechanisms (e.g., glue, clips, VELCRO™, etc.). A user may desire to remove heat transfer packs from heat transfer device housing for any number of reasons including, but not limited to, replacement of a heat transfer packs, cleaning the heat transfer device, and changing a size of an heat transfer packs. In some instances, different heat transfer packs may have different features or qualities that may incorporate functional, comfort, and/or decorative features. For example, a first heat transfer packs may be configured to reach a first temperature when chilled by a heat transfer machine while a second heat transfer packs may be configured to reach a second temperature when chilled by the heat transfer machine.

Surfaces for heat exchange for a heat transfer machine may be made from, for example, polyurethane foam R-6.3, polystyrene R-4, aerogel with R values up to 105, thermally insulated glass, copper, aluminum, and combinations thereof.

FIG. 1A provides and exemplary heat transfer system 100, that employs a Peltier device 105, a metal plate 110, a heat sink 115, a fan 120, a heat transfer device 125, and a housing 130. Peltier device 105 may be a thermal electric cooler that uses an electrical power input to create a temperature differential at a junction between two types of materials. This differential creates a potential for heat transfer to occur across the junction. Using the Peltier device 105, there is a maximum amount of heat that can be removed from a metal plate 110 and every Peltier device 105 has an input power point at which it is most efficient at transferring heat. Increasing the input power past this point produces enough heat within the Peltier device to counteract some of the work completed by the heat transfer process. On the other hand, going below the power point does not produce the optimum amount of heat transfer, as expected.

Heat sink 115 may be used to draw heat away from the hot side of the Peltier device 105 junction to prevent the heat from accumulating within the Peltier device 105. Fan 120 may be used to dissipate some of the heat stored in heat sink 115 into the surrounding environment. The placement of the components of heat transfer system 100 in the configuration of FIG. 1A enables heat to be drawn from metal plate 110 into heat sink 115.

Figure 1B:
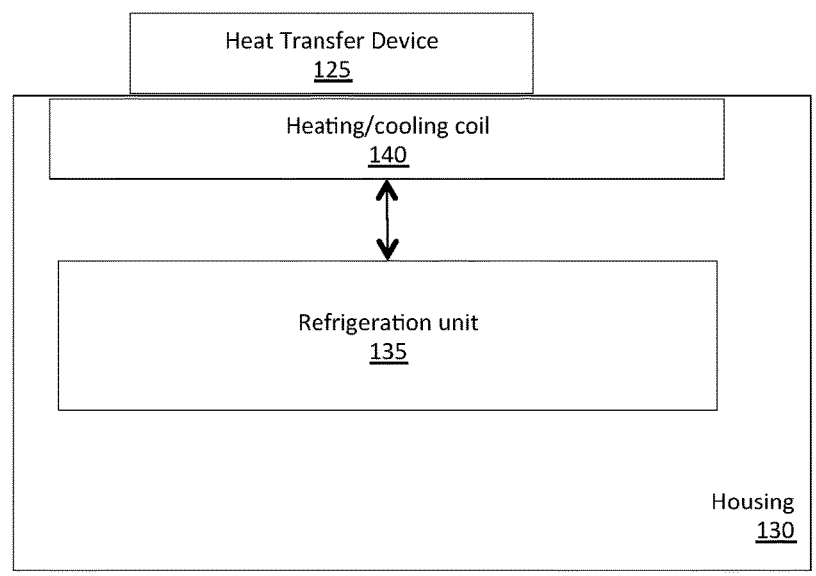

FIG. 1B provides another exemplary heat transfer system 101, which employs a housing 130, refrigeration unit 135 coupled to a cooling coil 140. The heating/cooling unit 135 and heating/cooling coil 140 are housed within housing 130 and an exemplary heat transfer device 125 is placed on an exterior surface of housing 130. In embodiments where heat transfer system 101 is designed to cool heat transfer device 125, h/c unit 135 may be a refrigeration unit that pumps cold liquid or gas through h/c coil 140 so that a portion of the exterior surface of housing 130 is cooled and heat may be transferred from heat transfer device 125 to housing 130 via placing heat transfer device 125 on housing 130. In embodiments where heat transfer system 101 is designed to heat transfer device 125, h/c unit 135 may be an electric heating coil or an induction heating device configured to warm the exterior surface of housing 120 and heat may be transferred to heat transfer device 125 to housing 130 via placing heat transfer device 125 on housing 130. In some embodiments, heat transfer system 101 may be configured to transfer heat both to and from heat transfer device 125 and these embodiments may include both a heating and a refrigeration apparatus.

Heat transfer systems 100 and/or 101 may be configured to be enclosed in a heat transfer machine. A heat transfer machine may be of any shape and/or size however, it will often be small enough to fit on, for example, a nightstand, a tabletop, or a counter in a user's residence. In most cases, heat transfer machine will be powered via a standard household electrical power supply although, in some instances, a battery that may be rechargeable may power heat transfer machine.

In some embodiments, the heat transfer machines described herein may be configured to monitor the state and/or temperature of a heat transfer device placed thereon and/or therein and may adjust one or more operations performed by a component of the heat transfer machine responsively to the monitoring. For example, when a heat transfer device has reached a desired temperature, heat transfer machine may be configured to turn off or cycle on and off so as to maintain the desired temperature of the heat transfer machine.

In other embodiments, a heat transfer machine and corresponding heat transfer device may be configured to as couple to one another in a manner that limits heat transference to and/or from the external environment. For example, in some instances there may be an air-tight seal between an heat transfer machine and its corresponding heat transfer device and in other instances, an heat transfer machine and/or heat transfer device may include a gasket or other coupling mechanism configured to limit heat transference to and/or from the external environment In some instances, the heat transfer machines described herein are sized and shaped to accommodate inclusion of and one or more components of heat transfer systems 100 and/or 101 therein. Heat transfer systems 100 and/or 101 may transfer heat to and/or from a heat transfer device via, for example, conduction (e.g., placing a heat transfer device proximate to a hot or cold surface of heat transfer systems 100 and/or 101) and/or convection (e.g., using a fan to cool and/or heat an heat transfer device).

Figure 2:
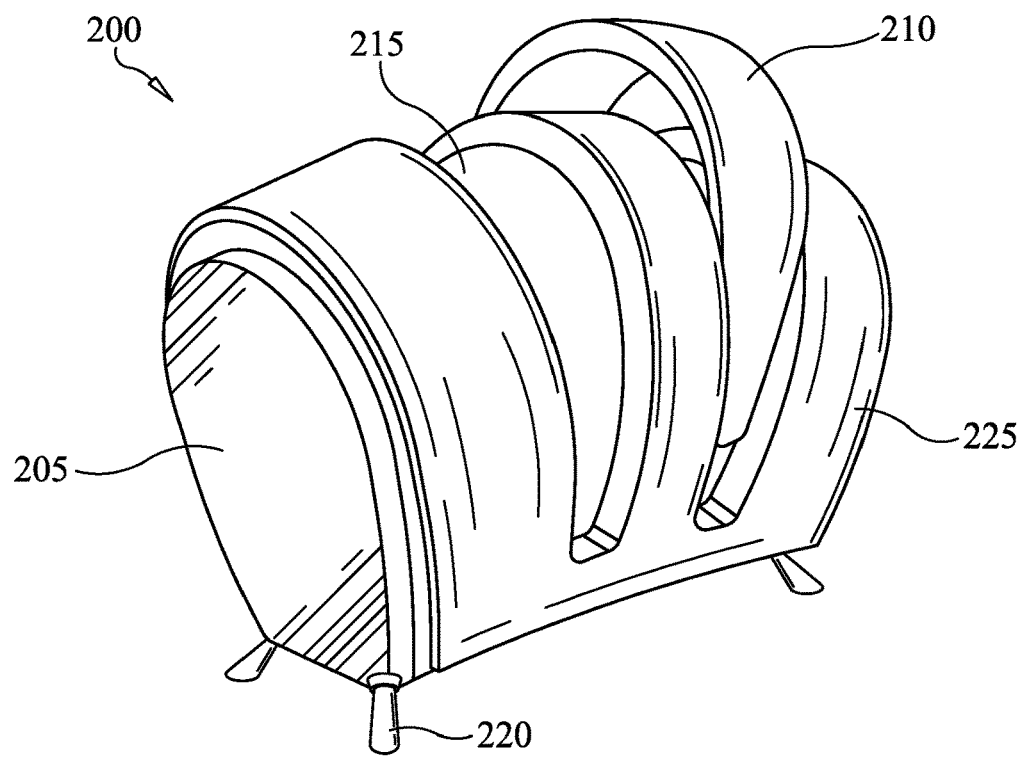
FIG. 2 is a block diagram of an exemplary heat transfer machine, in accordance with some embodiments of the present invention.

Additionally, or alternatively, the heat transfer machines described herein may be sized and shaped to accommodate positioning of one or more different heat transfer devices thereon or therein. For example, FIG. 2 provides an heat transfer machine 200 that includes a ventilation grate 205, a removable headband-shaped heat transfer device 210, a heat exchange surface 215, a support 220, and an exterior housing 225 configured to accommodate the shape and size of removable headband-shaped heat transfer device 210, which in the embodiment of FIG. 2 is shaped like a headband. Exterior housing 225 is shaped with a flat bottom and a curved upper surface that corresponds to the curvature of the headband-shaped heat transfer device 210.

Heat exchange surface 215 may be configured to transfer heat to and/or from headband-shaped heat transfer device 210 and, in some instances, may correspond to, for example, metal plate 110 and/or housing 130. In some instances, heat exchange surface 215 may be a surface or layer of material positioned above metal plate 110 and/or housing 130. In these instances, heat exchange surface 215 may be, for example, plastic or metal. In some embodiments, heat exchange surface 215 may be designed so as to limit the accumulation of condensation thereon. For example, heat exchange surface 215 may include a water absorbing material such as foam or fabric.

Ventilation grate 205 may be shaped so as to fit on either side end of exterior housing 225. Ventilation grate 205 may be configured to allow the passage of air through the heat transfer machine 200 so as to, for example, cool a heat sink such as heat sink 115 and/or a refrigeration unit such as refrigeration unit 135. In some embodiments, ventilation grate 205 may have a decorative pattern.

Figure 3:
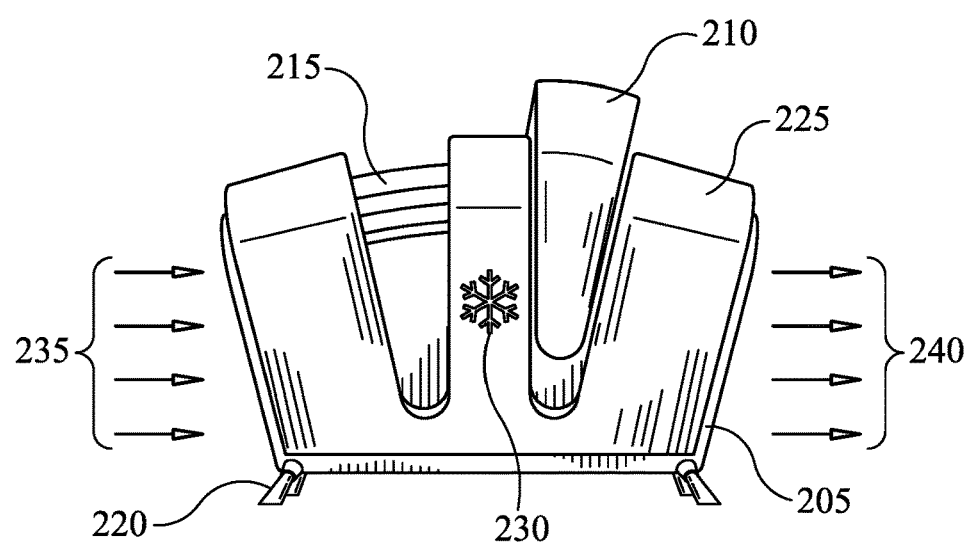
FIG. 3 provides a side plan view of an exemplary heat transfer machine, in accordance with some embodiments of the present invention.

FIG. 3 shows a side plan view of heat transfer machine 200. In this view of heat transfer machine 200, an indicator light 230 may be seen. Indicator light 230 may be configured to, for example, illuminate when a headband-shaped heat transfer device 210 is placed heat exchange surface 215 and/or when headband-shaped heat transfer device 210 has reached a desired temperature.

FIG. 3 also shows an incoming air flow 235 entering a first ventilation grate 205 and an outgoing air flow 240 as it second ventilation grate 205 of heat transfer machine 200 as may be the case when, for example, a fan, such as fan 120 draws air into heat transfer machine 200 so as to cool a heat sink, such a heat sink 115 and/or a refrigeration unit, such as refrigeration unit 135, and blows the air out of heat transfer machine 200.

Figure 4A:
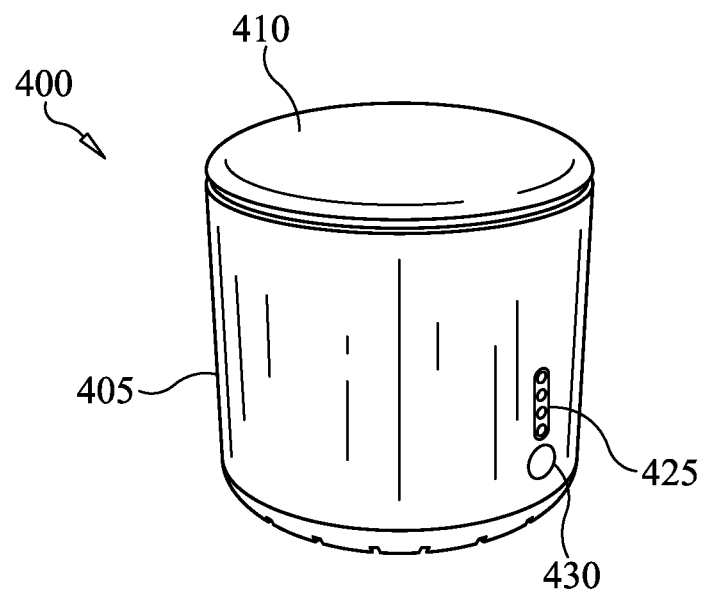
FIGS. 4A and 4B provide a diagram of exemplary heat transfer machine, in accordance with some embodiments of the present invention.
Figure 4B:
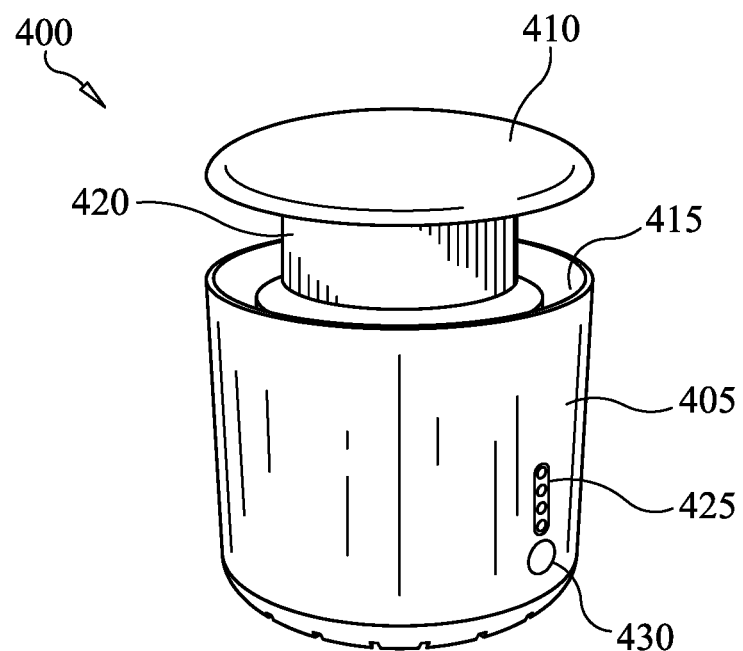

FIGS. 4A and 4B provide another exemplary heat transfer machine 400 that is substantially cylindrical in shape with a round cross section in at least one plane. FIG. 4A shows the heat transfer machine 400 when in a closed position and FIG. 4B shows the heat transfer machine 400 when in an open position. An exterior canister or container 405 provides a receiving space 415 into which a cooling canister 410 may be inserted. FIG. 4A shows the cooling canister 410 inserted into canister 405 (i.e., a closed position) and FIG. 4B shows the cooling canister 410 when extending from canister 405 (i.e., an open position).

A heat transfer system, such as heat transfer system 100 and/or 101 may be positioned within heat transfer machine 400 (not shown). In some embodiments, the heat transfer system may be positioned within cooling canister 405 and, in other embodiments, the heat transfer system may be posited within the receiving space 415 and cooling canister 410 may fit over top of or otherwise be coincident with, the heat transfer system.

Cooling canister 410 provides a heat transfer device heat transfer site 420, which may be shaped to as to accommodate positioning of one or more heat transfer device therein and/or thereon. The heat transfer system included in heat transfer machine 400 may be configured to provide heat transfer capabilities to the heat transfer device heat transfer site 420 so as to heat and/or cool a heat transfer device (not shown) positioned thereon and/or therein.

Cooling canister 410 may serve to collect any condensation caused by, for example, cooling a heat transfer device and/or heat transfer device heat transfer site 420 by, for example, insulating the heat transfer device and/or heat transfer device heat transfer site 420 from the ambient air/environment and/or providing a condensation collection device (e.g., a tray). In some embodiments, one or more rubber seal(s) and/or gasket(s) between the cooling canister 410 and the exterior canister 405 may effect insulating the cooling canister 410 from the ambient air. The one or more rubber seal(s) and/or gasket(s) may also provide a snug fit between the exterior canister 405 and the cooling canister 410. Additionally, or alternatively an exterior surface of the exterior canister 405 may be textured to create a visual or tactile impression for the user.

Heat transfer device 400 may provide electronics that regulate the temperature of the cooling canister 410 and/or a heat transfer device placed thereon or therein. These electronics may be coupled to, for example, power on/off button 430 and/or a visual indicator 425. Power on/off button 430 may serve to power the heat transfer machine 400 on and/or off and visual indicator 425 may act to provide a visual indicator of for example, the temperature and/or degree of readiness of the heat transfer device and/or the cooling canister 410. Visual indicator 425 may be, for example, a light that changes color, a series of lights, etc.

In many instances, heat transfer machine 400 may be used when a heat transfer device is placed in or on heat transfer device heat transfer site 420 when heat transfer machine is in an open configuration as shown in FIG. 4B and heat transfer machine 400 is then closed (as shown in FIG. 4A). For example, a headband-shaped heat transfer device and/or a heat transfer device to be placed in a housing may be placed in heat transfer device heat transfer site 420 when heat transfer machine is in an open configuration and then, when the heat transfer machine is placed in a closed configuration, heat transfer machine may begin transferring heat to and/or from the heat transfer device.

Figure 5:
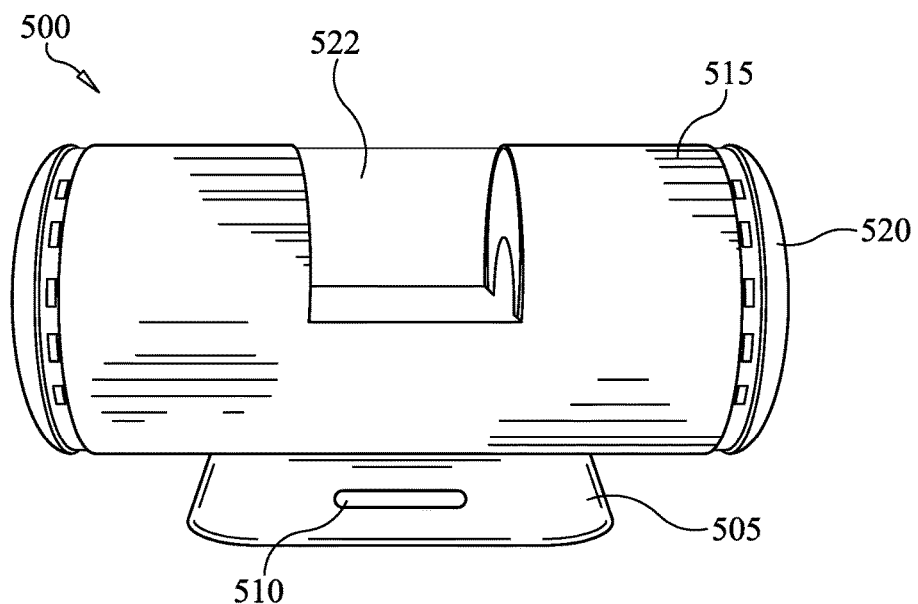
FIGS. 5-7 provide various views of an alternate exemplary heat transfer machine, in accordance with some embodiments of the present invention.
Figure 6:
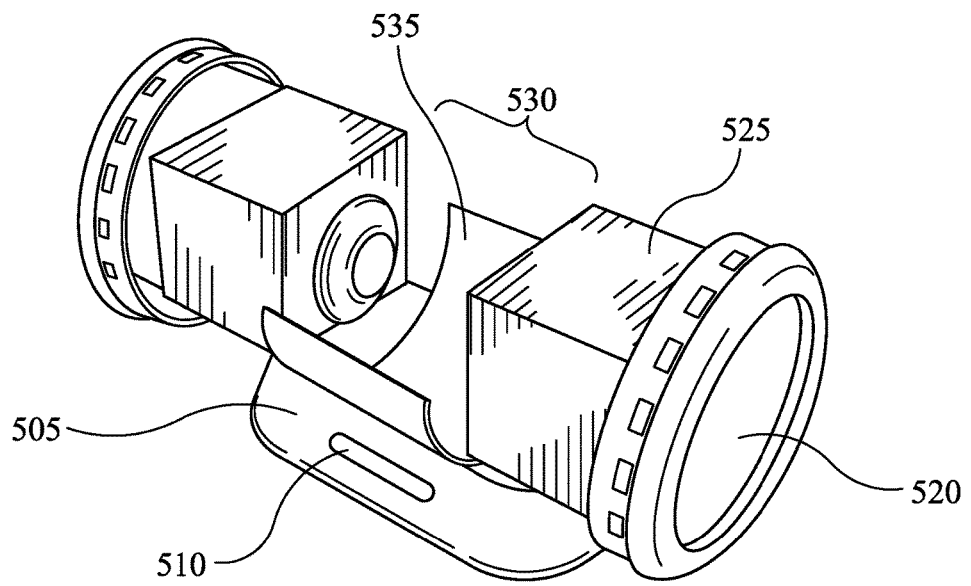
Figure 7:
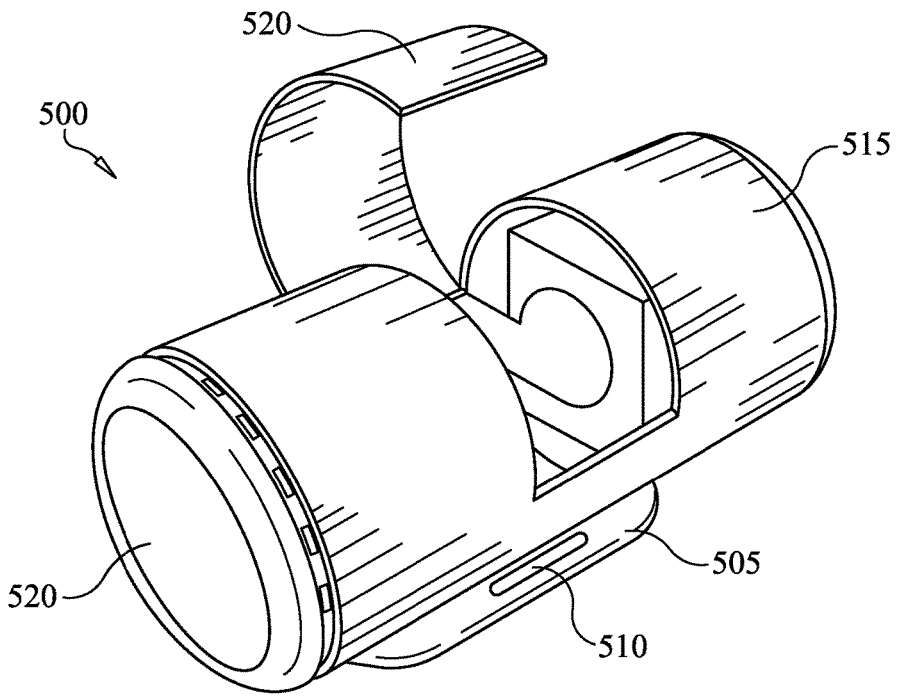

FIGS. 5-7 provide various views of an alternate exemplary heat transfer machine 500 with FIG. 5 being a front plan view of an assembled heat transfer machine 500 with a closed heat transfer device access door, FIG. 6 being a side perspective view of a partially assembled heat transfer machine 500, and FIG. 7 being a side perspective view of an assembled heat transfer machine 500 with an open heat transfer device access door. Heat transfer machine 500 includes a stand 505, a visual indicator 510, an exterior canister 515, an end cap 520, and a heat transfer device access door 522, an opening 530 to accommodate insertion and/or removal of an heat transfer device, a heat transfer surface 535, and heat transfer system components 525. Exterior canister 515 may house the components of heat transfer machine 500.

Heat transfer machine 500 may operate by opening heat transfer device access door 520, inserting a heat transfer device into opening 530 so that it is in contact with heat transfer surface 535, and closing the heat transfer device access door 520 and turning the heat transfer machine 500 on and/or setting a desired temperature for the heat transfer device placed in the heat transfer machine 500. Heat transfer system components 525 may act to change and/or regulate the temperature of heat transfer surface 535 according to, for example, one or more user-configured and/or default instructions in a manner similar to heat transfer machines 300 and 400.

Figure 8:
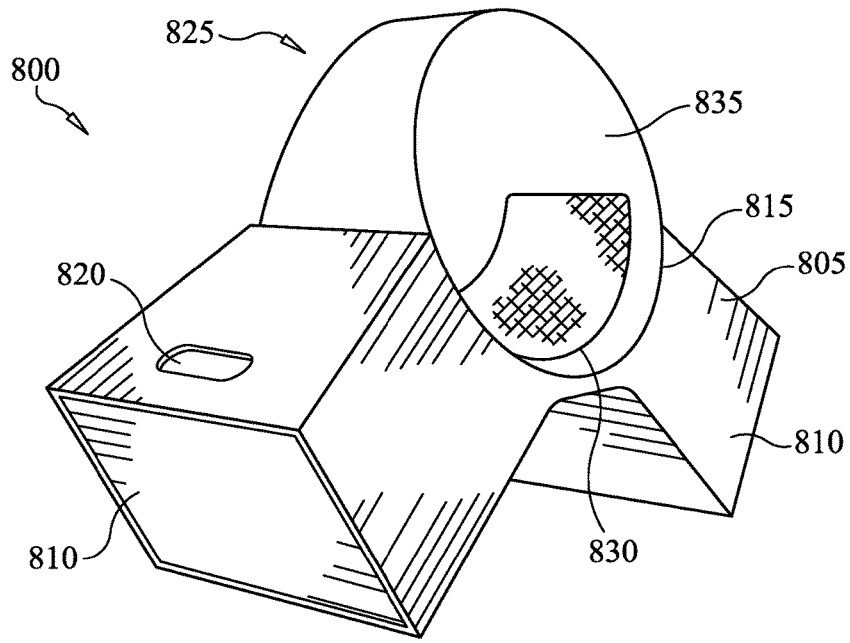
FIG. 8 is provides an exemplary heat transfer machine, in accordance with some embodiments of the present invention.

FIG. 8 shows yet another exemplary heat transfer machine 800 with an exemplary heat transfer device 825 placed thereon. Heat transfer machine 800 includes a base 805 with two legs oriented at an angle (e.g., 30-70°) with respect to a surface upon which heat transfer machine 800 rests. Base 805 may house one or more heat transfer system 100 and/or 101 (not shown) that are configured to transfer heat to and/or from a heat transfer device 825 positioned within a cradle 815 provided by based 805. Cradle 815 may be sized and/or positioned to accommodate positioning of one or more heat transfer devices 825 thereon or therein. An exterior surface of cradle 815 may transfer heat to and/or from heat transfer device 825 positioned thereon/therein via conduction and/or convection.

Base 805 may include one or more ventilation grids 810 via which air may be pulled into and/or pushed out of base 805 by, for example, a fan included in heat transfer system 100 and/or 101. Base 805 may further include an indicator mechanism 820 that may serve to indicate to a user that the heat transfer machine 800 is on and/or off.

Heat transfer device 825 includes an exemplary heat transfer pack 830 and a heat transfer device housing 835. In the embodiment of FIG. 8, housing 835 has a circular shape that may be worn, for example, on a part of a mammal with a relatively large diameter/cross section (e.g., head, torso, upper leg, etc.) and heat transfer pack 830 is positioned on an interior surface of housing 835.

Figure 9:
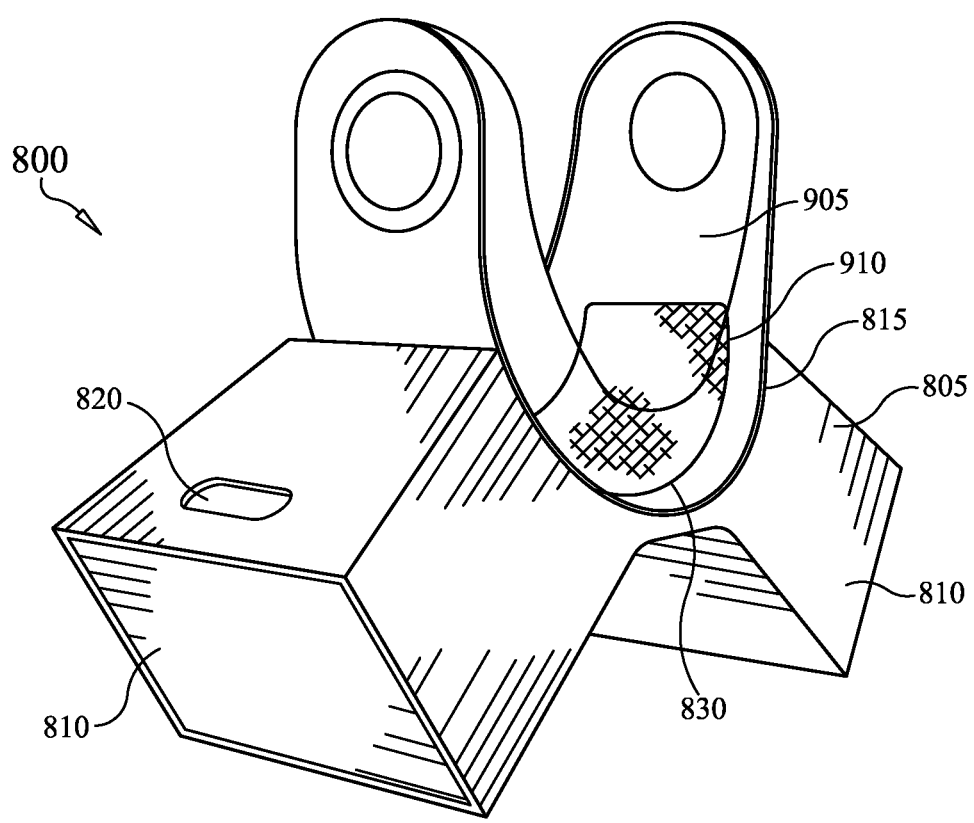
FIG. 9 is provides an exemplary heat transfer machine, in accordance with some embodiments of the present invention.

FIG. 9 shows heat transfer machine 800 with another exemplary heat transfer device 905 placed thereon. The housing 915 of heat transfer device 905 has a semicircular shape that may be conducive to use on a curved surface of mammalian skin (e.g., a head or leg). Heat transfer device 905 includes a heat transfer pack 910.

Figure 10:
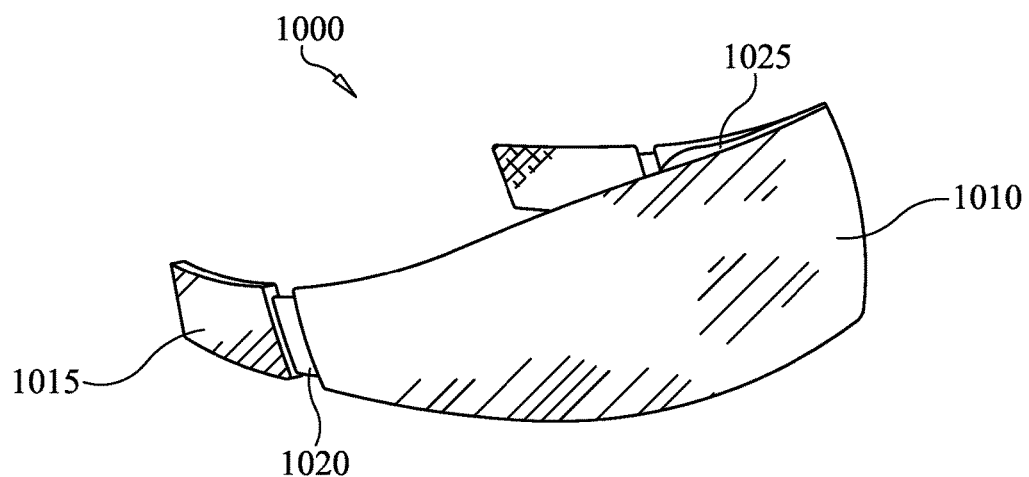
Figure 11:
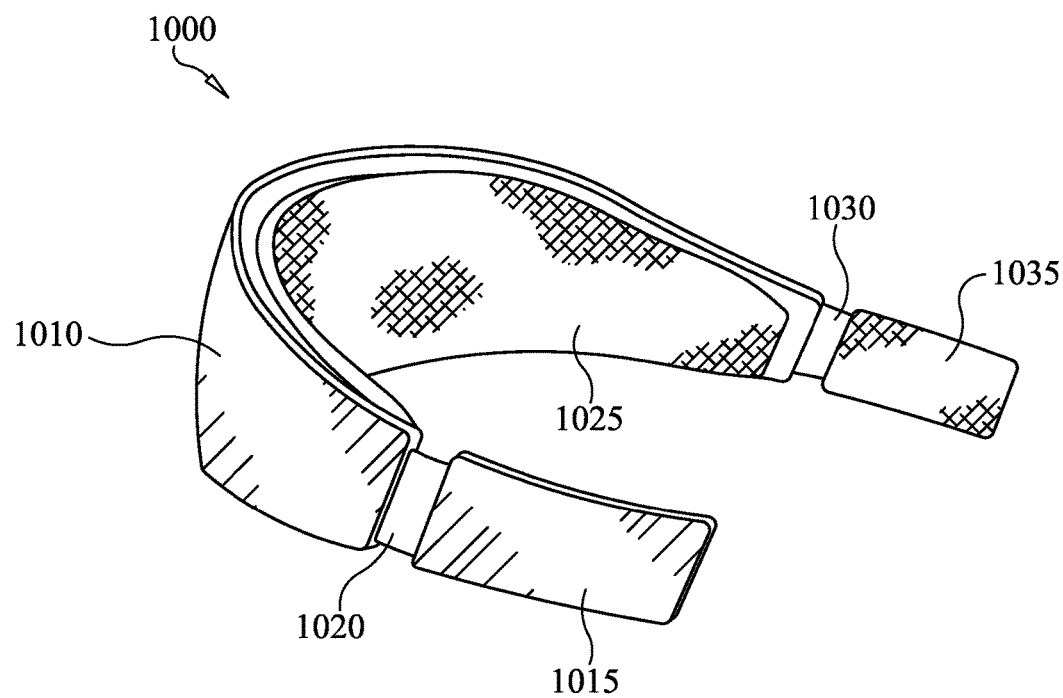

FIGS. 10-12 provide exemplary heat transfer devices 1000 configured to be worn on a person's head, and more specifically on across a person's forehead above the eyebrows and below the hairline. Heat transfer devices 1000 may include a housing 1010, two side extensions 1015, a slide bar 1020, a heat transfer pack 1025, a first liner 1030, and a second liner 1035. Housing 1010 may be configured to, for example, provide a structural shape to heat transfer devices 1000 and/or insulate the heat transfer pack from ambient air. First liner 1030 may be configured to provide padding to the heat transfer devices 1000 and assist conforming the shape of heat transfer devices 1000 to the shape of the person's head to which it is applied. Heat transfer pack 1025 may be designed to come into contact with a portion of the person's head and transfer heat to and/or from the person's skin and, in some instances, tissue underlying the skin.

One or more components of Heat transfer devices 1000 may be adjustable so as to, for example, improve the fit of heat transfer devices 1000 when worn. For example, a positioning of side extensions 1015 may be adjusted and/or modified by sliding one, or both, side extensions 1015 away from and/or toward the main body of heat transfer devices 1000 along slide bar 1020. Second liner 1035 may act to facilitate comfortable compression of side extensions 1015 and/or housing 1010 onto a wearer's skin as shown in FIG. 12.

Figure 13C:
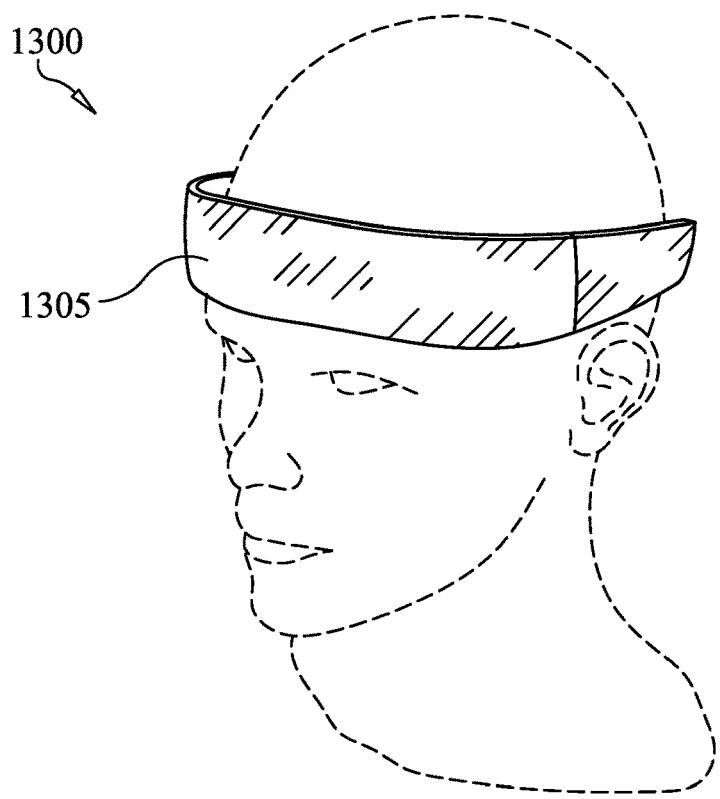

FIGS. 13A-13B provide different views of another exemplary heat transfer devices 1300 configured to be worn on a person's head, and more specifically on across a person's forehead above the eyebrows and below the hairline. Heat transfer devices 1300 may include a housing 1305, a heat transfer pack 1310, two side extensions 1315, a pad 1320, and a hinge 1325.

Figure 13D:
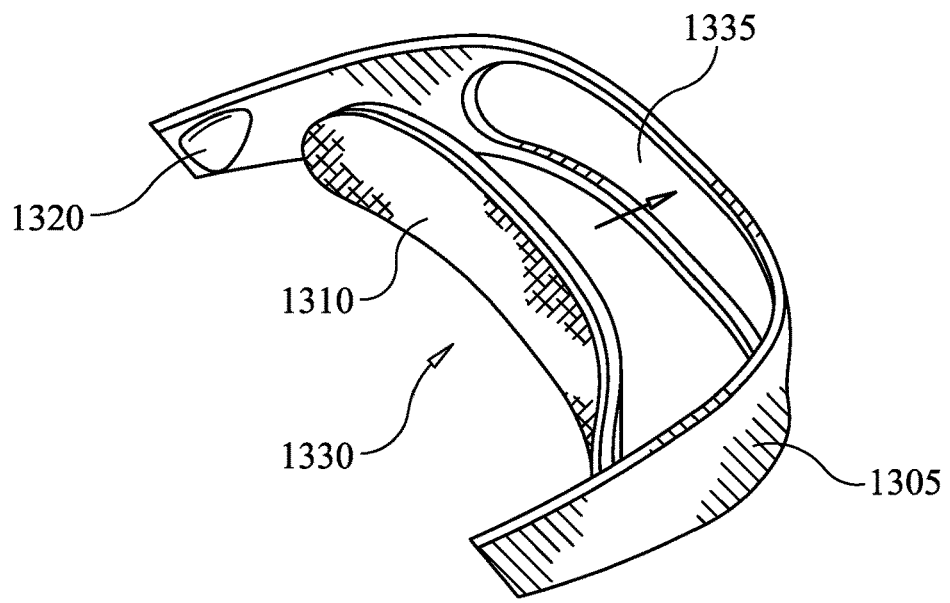

Housing 1305 may be configured to, for example, provide a structure and shape to heat transfer devices 1300 and/or insulate heat transfer pack 1310 from ambient air. As can be seen in FIG. 13D, heat transfer pack 1310 may be a component of an heat transfer pack assembly 1330 that may be removed from and/or inserted into housing 1305 via an opening 1335 in housing 1305. Heat transfer pack assembly 1330 may be removably affixed to housing 1305 via, for example, a friction mechanism or a mechanical structure such as a tongue and groove arrangement or a plurality of tabs or clips. Heat transfer pack assembly 1330 may be removed from housing 1305 so as to, for example, replace a first heat transfer pack assembly 1330 with a second Heat transfer pack assembly 1330 or to place heat transfer pack assembly 1330 in contact with a heat transfer machine as described above. In the embodiment of FIG. 13D, heat transfer pack assembly 1330 may include heat transfer pack 1310 and a layer of material that is the same as and/or similar to the material used to fabricate housing 1305.

Figure 14A:
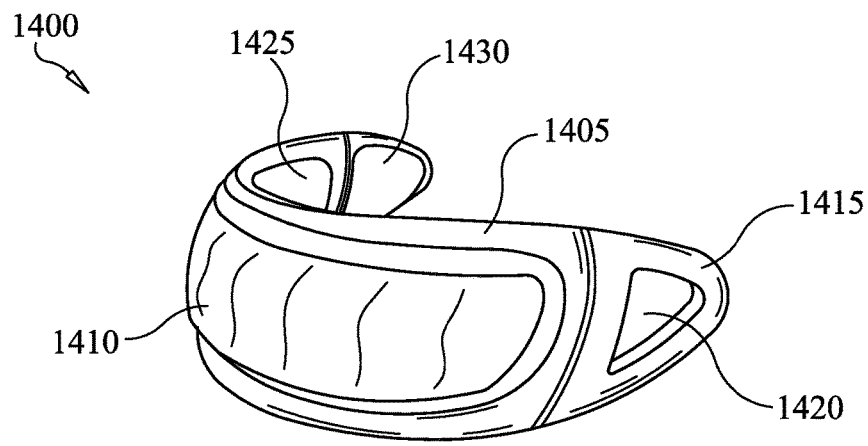
FIGS. 14A-14B provide different views of another exemplary heat transfer devices, in accordance with some embodiments of the present invention.
Figure 14B:
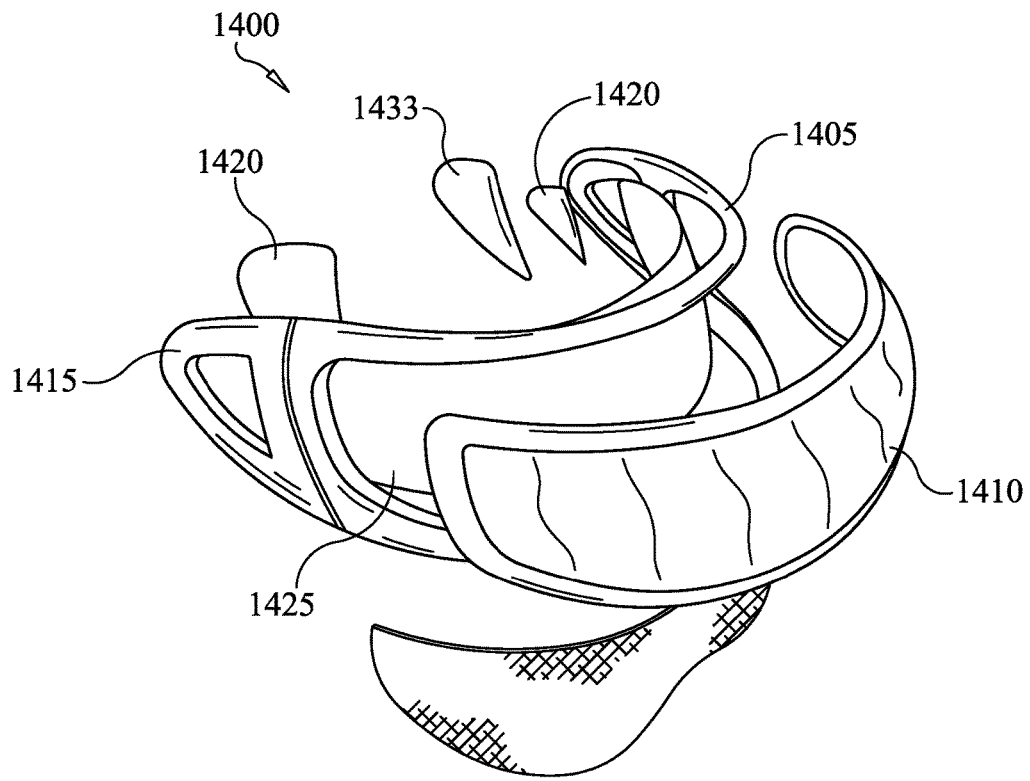

FIGS. 14A-14B provide different views of another exemplary heat transfer devices 1400 configured to be worn on, for example, a person's head or another curved surface of mammalian skin. Heat transfer devices 1400 may include a housing 1405, a first heat transfer pack 1410, two side extensions 1415, a second heat transfer pack 1420, a liner 1425, and a side pad 1430.

Housing 1405 may be configured to, for example, provide a structure and shape to heat transfer devices 1400, insulate heat transfer pack 1410 from ambient air, and/or provide a place in which to insert heat transfer pack 1410. Heat transfer pack 1410 may be removably affixed to housing 1405 via, for example, a friction mechanism or a mechanical structure such as a tongue and groove arrangement or a plurality of tabs or clips. Heat transfer pack 1410 may be removed from housing 1405 so as to, for example, replace a first heat transfer pack 1410 with a second heat transfer pack 1410 or to place heat transfer pack 1410 in contact with a heat transfer machine as described above. Heat transfer device 1400 includes a liner 1425 that may be adapted to insulate heat transfer pack 1410 from the heat of a mammal's skin to which it may be applied.

Figure 15A:
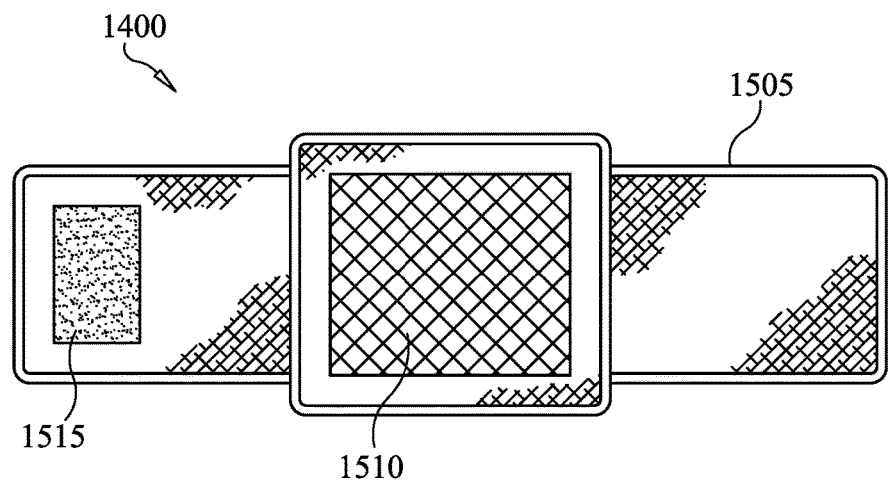
FIGS. 15A and 15B provide an exemplary heat transfer device, in accordance with some embodiments of the present invention.
Figure 15B:
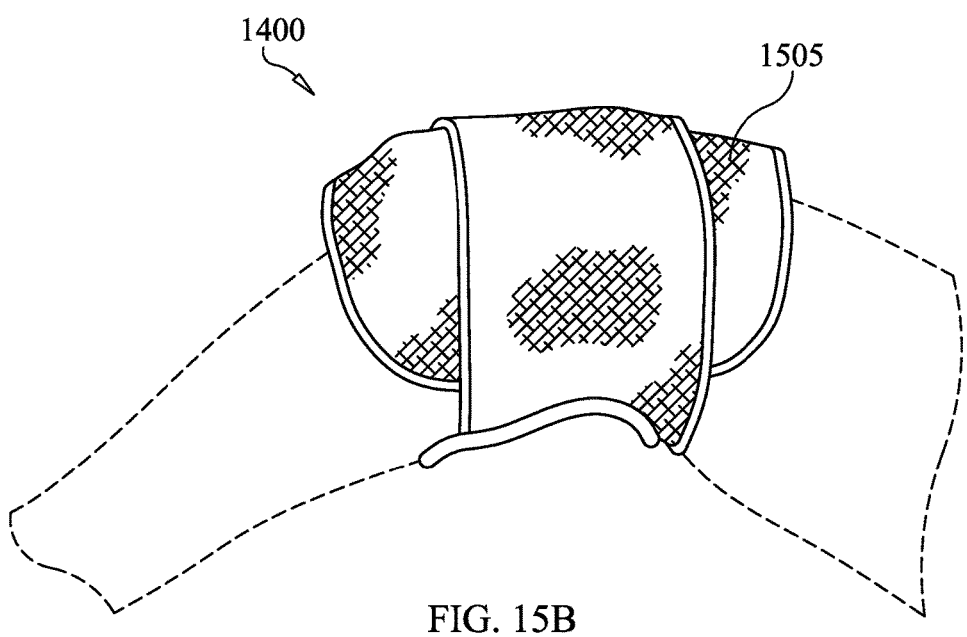

FIGS. 15A and 15B provide an exemplary heat transfer device 1500 in the form of a wrap for a mammalian limb (e.g., arm or leg) or torso that includes a housing 1505, a heat transfer pack 1510, and an attachment mechanism 1515. Heat transfer pack 1510 may be adapted to be cooled and/or heated via, for example, placement on a heat transfer device as described herein. In some embodiments, heat transfer pack 1510 maybe removed from housing 1505 for heating/cooling via a heat transfer device and then affixed to and/or placed in housing 1505.

Housing 1505 may be used to, for example, facilitate placement of heat transfer pack 1510 on a desired body part and maintenance of the heat transfer pack's 1510 placement on the desired body part. In one example, the desired mammalian body part is a human knee. The housing 1505 may be employed to place the heat transfer pack in a desired position relative to the user's knee and wrap around the user's knee. Heat transfer device 1500 may be held in place via attachment mechanism 1515 as shown in FIG. 15B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I claim:

1. A heat transfer system comprising:
   a heat transfer machine adapted to thermally couple to a heat transfer pack housed within an heat transfer device and transfer heat from the heat transfer pack using electrical power provided by a power supply; and
   the heat transfer device comprising:
      the housing adapted to house the heat transfer pack and conform to a portion of a mammal's skin; and
      the heat transfer pack, the heat transfer pack being adapted to thermally couple to the heat transfer machine, transfer heat to the heat transfer machine while thermally coupled and removably attached to the heat transfer machine, and transfer heat from a mammal's skin when the heat transfer device uncoupled from the heat transfer machine and is in contact with the mammal's skin.

2. The heat transfer system of claim 1, wherein the heat transfer pack is removably attached to the heat transfer device.

3. The heat transfer system of claim 1, wherein the heat transfer machine is adapted to transfer heat to the heat transfer pack and the heat transfer pack is adapted to transfer heat to the mammal's skin.

4. The heat transfer system of claim 1, wherein the heat transfer machine comprises:
   a Peltier device;
   a metal plate;
   a heat sink adapted to absorb heat from the Peltier device; and
   a fan adapted to dissipate heat from the heat sink; and
   a power supply.

5. The heat transfer system of claim 1, wherein the heat transfer pack comprises one or more phase change materials.

6. The heat transfer system of claim 1, wherein the heat transfer pack is positioned on an external surface of the heat transfer machine.

7. The heat transfer system of claim 1, wherein the heat transfer pack is cooled to a temperature within the range of 1° C. and 9° C.

8. The heat transfer system of claim 1, wherein the heat transfer pack maintains its temperature for at least 20 minutes when in contact with the mammal's skin.

9. The heat transfer system of claim 1, wherein the heat transfer pack maintains its temperature for no more than three hours when in contact with the mammal's skin.

10. The heat transfer system of claim 1, wherein the heat transfer pack is not electrically coupled to the heat transfer machine.

11. The heat transfer system of claim 1, wherein the heat transfer machine is adapted to power off when the heat transfer pack is no longer thermally coupled to the heat transfer machine.

12. The heat transfer system of claim 1, wherein the heat transfer device is configured to be worn on at least one of a mammal's head, arm, leg, torso, hand, and foot.

13. The heat transfer system of claim 1, wherein the heat transfer machine is adapted to transfer heat from the heat transfer pack via conduction.

14. The heat transfer system of claim 1, wherein the heat transfer device is adapted to cool the mammal's skin without being coupled to a power supply.

15. The heat transfer system of claim 1, wherein the heat transfer machine is adapted to transfer heat from the heat transfer pack and thereby achieve a desired temperature for the heat transfer pack within a range of 1 to 10 hours.

16. An heat transfer device comprising:
   a housing adapted to house an heat transfer pack and conform to a portion of a mammal's skin; and
   the heat transfer pack, the heat transfer pack being adapted to thermally couple and removably attach to a heat transfer machine, transfer heat to the heat transfer machine while thermally coupled to the heat transfer machine, and transfer heat from a mammal's skin when the heat transfer device is uncoupled from the heat transfer machine and in contact with the mammal's skin.

17. The heat transfer device of claim 16, wherein the heat transfer pack is removably attached to the heat transfer device.

18. The heat transfer system of claim 16, wherein the heat transfer pack comprises one or more phase change materials.

19. The heat transfer system of claim 16, wherein the heat transfer pack is cooled to a temperature within the range of 1° C. and 9° C.

20. The heat transfer system of claim 16, wherein the heat transfer pack maintains its temperature for at least 20 minutes when in contact with the mammal's skin.

21. The heat transfer system of claim 16, wherein the heat transfer pack maintains its temperature for no more than three hours when in contact with the mammal's skin.

22. The heat transfer system of claim 16, wherein the heat transfer pack is not electrically coupled to the heat transfer machine.

23. The heat transfer system of claim 16, wherein the heat transfer device is configured to be worn on at least one of a mammal's head, arm, leg, torso, hand, and foot.

24. The heat transfer system of claim 16, wherein the heat transfer machine is adapted to transfer heat from the heat transfer pack via conduction.

25. The heat transfer system of claim 16, wherein the heat transfer device is adapted to cool the mammal's skin without being coupled to a power supply.

26. The heat transfer system of claim 16, wherein the heat transfer machine is adapted to transfer heat from the heat transfer pack and thereby achieve a desired temperature for the heat transfer pack within a range of 1 to 10 hours.

27. The heat transfer system of claim 16, wherein the heat transfer pack is thermally coupled to an external surface of the heat transfer machine.

\* \* \* \* \*